United States Patent

Lasner et al.

[11] 4,271,838
[45] Jun. 9, 1981

[54] SUTURE CUTTER

[75] Inventors: Jeffrey I. Lasner, Yonkers; Francisco H. Aleixo, Tarrytown, both of N.Y.

[73] Assignee: Laschal Instruments Corp., North Tarrytown, N.Y.

[21] Appl. No.: 945,809

[22] Filed: Sep. 26, 1978

Related U.S. Application Data

[63] Continuation-in-part of Ser. No. 893,582, Apr. 5, 1978, abandoned, which is a continuation-in-part of Ser. No. 872,388, Jan. 26, 1978, abandoned.

[51] Int. Cl.³ .................. A61B 17/32; B25F 3/00; B26B 1/00
[52] U.S. Cl. .................... 128/318; 30/124; 30/134; 30/131
[58] Field of Search .............. 128/305, 321, 318; 30/124, 134, 131, 135; 81/418, 425 A, 425 R, 426

[56] References Cited

U.S. PATENT DOCUMENTS

| | | | |
|---|---|---|---|
| 2,025,345 | 7/1935 | Harris | 128/318 |
| 2,765,532 | 7/1956 | Fruit | 30/254 |
| 2,865,099 | 8/1958 | Blackwood | 30/134 |
| 3,266,493 | 8/1966 | Cummings | 128/318 |
| 3,328,876 | 7/1967 | Hoppe | 30/124 |
| 3,364,572 | 8/1968 | Hoppe | 30/124 |
| 3,443,313 | 5/1969 | Profy | 30/134 |
| 3,585,985 | 6/1971 | Gould | 128/2 |
| 3,651,811 | 3/1972 | Hildebrandt et al. | 128/303.17 |
| 4,011,870 | 3/1977 | Goldstein | 128/276 |
| 4,026,295 | 5/1977 | Lieberman | 128/305 |
| 4,034,373 | 7/1977 | May | 30/181 |
| 4,043,343 | 8/1977 | Williams | 128/321 |
| 4,053,979 | 7/1977 | Tuthill et al. | 128/318 |
| 4,098,157 | 7/1978 | Doyle | 83/13 |

Primary Examiner—Robert W. Michell
Assistant Examiner—C. W. Shedd
Attorney, Agent, or Firm—Bierman & Bierman

[57] ABSTRACT

A suture cutter comprising a member and a blade, said blade having a knife edge and a back remote from said edge, said blade being adapted to shearingly contact said member, said member having a depth and comprising an arm, an element, and a slot therebetween, said slot having a portion adapted to receive a suture but being too small to permit a knot in said suture to pass therethrough, whereby shearing contact between said member and said blade cuts said suture leaving a stub on the side of said suture away from the tissue in which said suture is tied substantially equal in length to said depth.

Variations of the foregoing device are also disclosed, including forms in which the motion between the member and the blade is obtained by a scissor-like action as well as by a tweezer-like action; in addition, an embodiment wherein the handles or gripping area of the device is in a different plane from the working end. There is also disclosed a combination of the present invention with a surgical needle holder.

18 Claims, 11 Drawing Figures

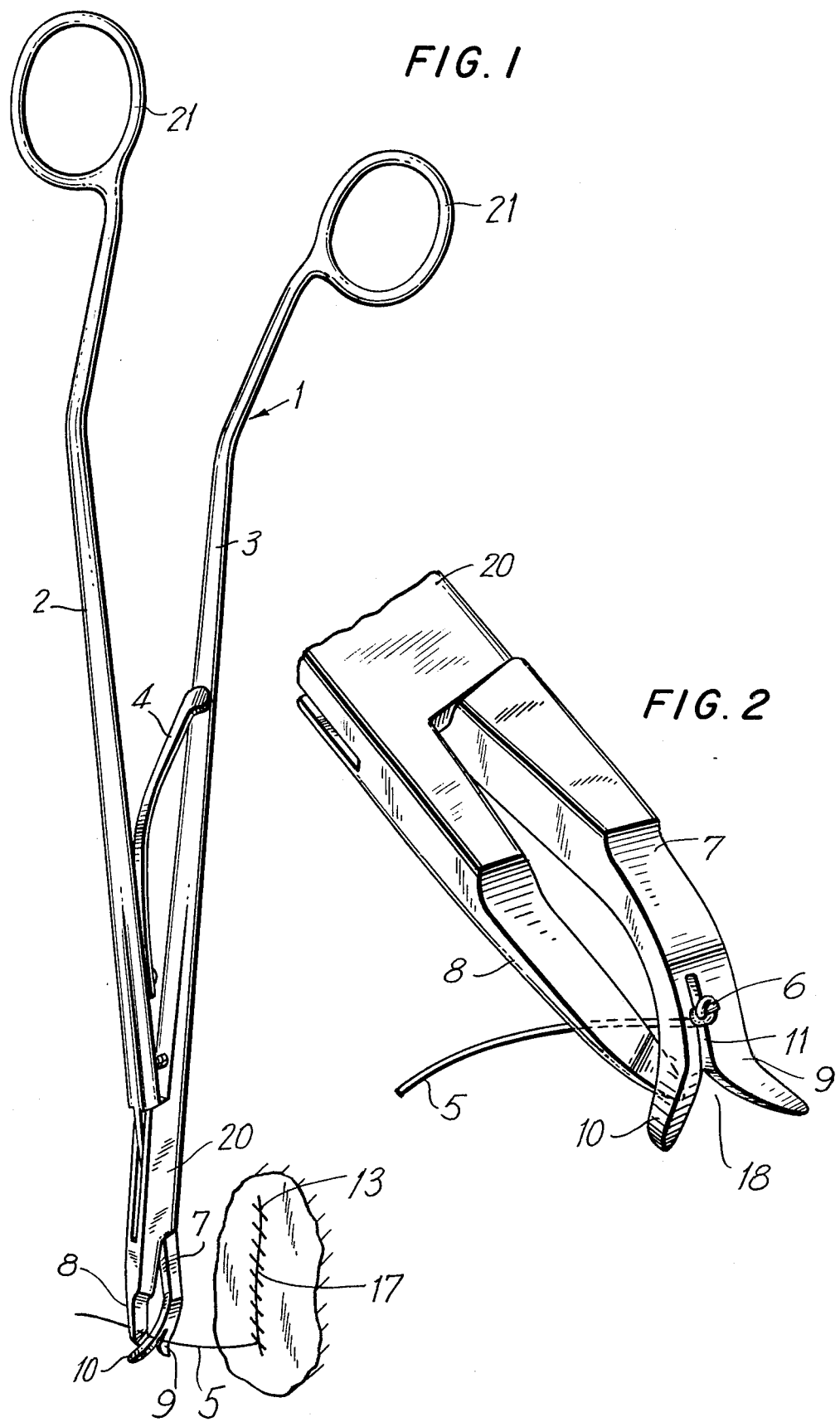

SUTURE CUTTER

This application is a continuation-in-part of Ser. No. 893,582, filed Apr. 5, 1978, now abandoned which is a continuation-in-part of Ser. No. 872,388, filed Jan. 26, 1978 now abandoned.

The present invention is directed to an improvement in surgical instruments, more specifically to suture cutters.

Suture cutters as such have been known in the art for many years. They are used to sever the end of the suture after the surgeon has knotted it. A predetermined length of stub should be left for best results. If the stub is too short, there is a danger that the knot will loosen. If the stub is too long, it may interfere with surrounding tissues. Therefore, getting the length correct is one of the problems of the surgeon.

In addition, since sutures are usually tied inside the body, the risk of cutting tissue or a blood vessel is quite substantial. The surgeon must exercise considerable care in order to avoid doing this. The problem is compounded when the suture is deep in the body or the patient is particularly obese.

The present invention is intended to overcome the deficiencies of the prior art, and to provide a suture cutter which is simple and virtually foolproof in its operation. By the proper use of the present invention, even a semi-skilled assistant can cut the sutures quickly, easily, and safely.

In practicing the present invention, there is provided a suture cutter comprising a first shank and a second shank. The shanks are pivotally connected to one another at a point intermediate their ends, thus forming a scissor-like arrangement. One end of the pair of shanks constitutes a handle. The first shank terminates in a member at the end thereof remote from the handle and the second shank terminates in a blade at the end remote from the handle. The blade is provided with a knife edge and a back remote from the edge. In this manner, the blade is adapted to shearingly contact the member.

The member itself is of a predetermined depth and comprises an arm, an element, and a slot therebetween. The slot is large enough to receive the suture but is too small to permit a knot in the suture to pass therethrough.

The blade and knife edge contact the element on the "top" or side away from the incision. As a result, the depth of the member determines the length of stub which will be left after cutting.

In a preferred form of the device, the arm is relatively rigid and the element is flexible. Therefore, the element is capable of moving towards the arm as the blade rubs against it during the cutting operation. This causes, in the most preferred form of the device, the element to contact the arm and secure the suture within the slot. For best results, the element should be spring biased away from the arm and a hole provided in the slot to receive the suture. The hole, like the slot itself, is too small to permit a knot in the suture to pass through.

For best results and simplest operation, the slot is provided with an access opening so that the suture can be readily inserted. It is particularly helpful if the access opening is flared for ease of insertion of the suture.

An advantageous form of the device includes a face on the blade located adjacent the surface of the element. The face is inclined toward the element so that the portion of the face near the knife edge is further from the element than the portion near the back. As a result, the pressure on the element increases as the knife edge moves over the element and cuts the suture. This insures that the element closes the slot and holds the suture in position.

The operation of the instrument is extremely simple and foolproof. After the surgeon has tied the suture knot, the free suture is inserted into the slot through the flared opening. This can be done near the upper end of the suture for convenience. The instrument is then slid down along the suture until the underside of the member contacts the knot. The handles are then brought together in the usual manner, and the knife edge cuts the suture.

As can easily be seen, the depth of the member determines the length of the stub of suture which will be left. Therefore, it is only necessary to design the cutter so that the member has a thickness corresponding to the desired length of suture stub. For example, 3 to 3.5 mm is appropriate for silk sutures, 4.5 to 5 mm is proper for gut, etc.

As a modified method of using the device, the instrument may be partially closed before sliding it along the suture so that the blade bears against the element and causes it to close the slot. The suture is held in the hole by this means. In this way, there is no real chance that the suture can slip out of the slot.

In another modification of the present invention, the suture cutter is mounted on the same "forceps" as constitute a surgical needle holder. Thus, without changing instruments or releasing the knot he is tying, the surgeon can make the stitch, tie the knot, and cut off the excess suture leaving precisely the correct amount of stub.

As can be seen from the foregoing, it is virtually impossible for the surgeon to inadvertently cut any tissue, blood vessels, organs, etc. In fact, the suture can be safely cut even if the surgeon cannot see the knot.

In the accompanying drawings, constituting a part hereof and in which like reference characters indicate like parts, FIG. 1 is an overall view of the device, partly diagrammatic;

FIG. 2 is an enlarged bottom view in perspective of the operative portion of the device;

Figure 3:
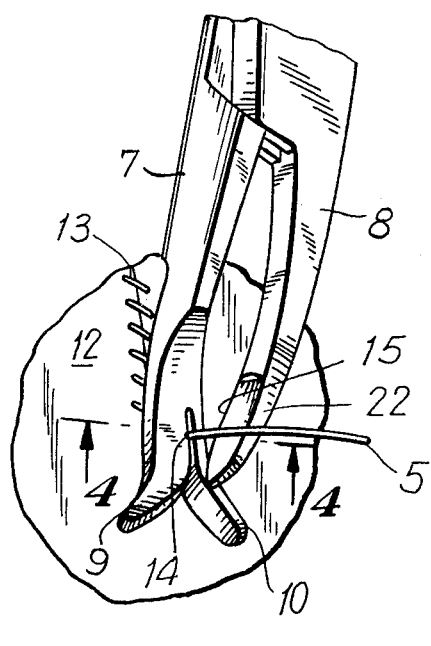
FIG. 3 is an enlarged top view of the operative portion of the device as it is used.
Figure 5:
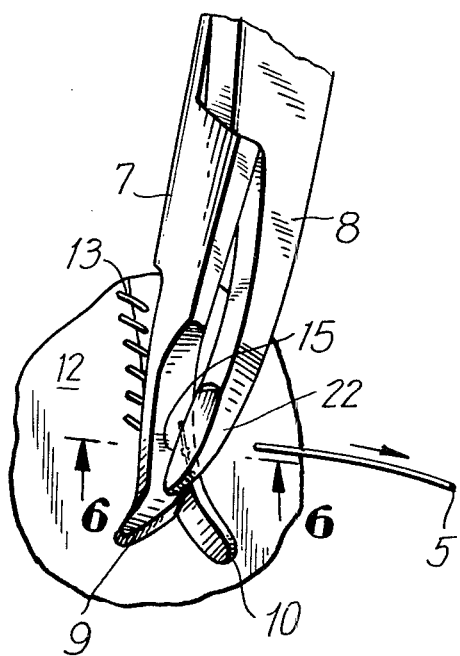
FIG. 5 is a view similar to FIG. 3 after the suture has been cut.

The suture cutter of the present invention is shown generally at 1. It comprises a first shank 2 and a second shank 3. Shanks 2 and 3 are pivotally connected at point 20 intermediate their ends. Spring 4 is provided to bias cutter 1 in its open position.

Shank 3 terminates, on the opposite side of point 20 from handle 21, in blade 8 having a knife edge 15. Shank 2 terminates at the end opposite handle 21, in member 7.

Member 7 bifurcates adjacent its end into arm 9 and element 10. Knife edge 15 is adapted to pass shearingly over element 10 and arm 9 to cut suture 5 which is placed in hole 14 in slot 11. Access opening 18 is provided at the end of slot 11 so that suture 5 can easily be inserted therein.

Figure 4:
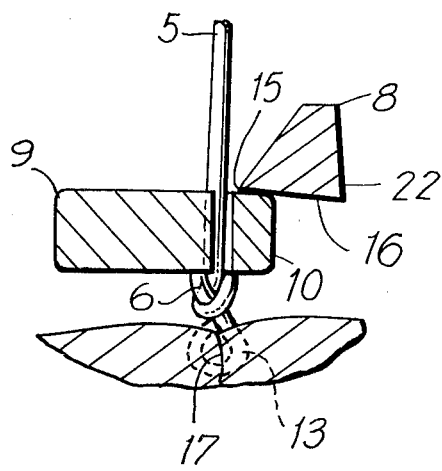
FIG. 4 is a cross-sectional view along line 4—4 of FIG. 3.
Figure 6:
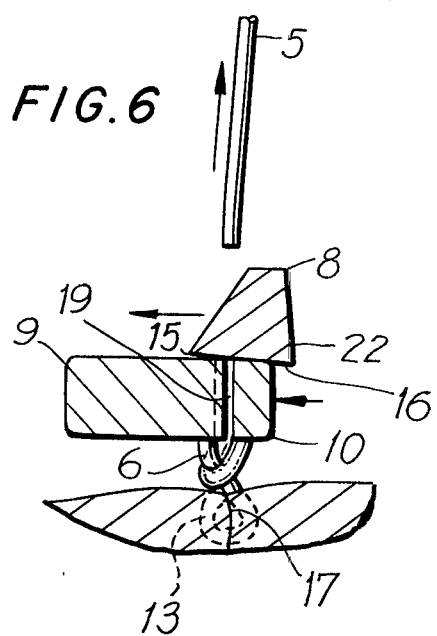
FIG. 6 is a cross-sectional view along line 6—6 of FIG. 5.

Referring more specifically to FIGS. 4 and 6, face 16 of blade 8 is inclined with respect to element 10. Thus, as blade 8 is moved towards suture 5, the pressure of face 16 on element 10 is increased. This insures that element 10 will move to the position shown in FIG. 6 and hold suture 5 securely as it is being cut. After cutting, stub 19 is left on suture 5.

In using the instrument, incision 17 is closed by a means of stitches 13 in skin 12. Before cutting, suture 5 extends from each stitch. Suture 5 is then inserted into slot 11 and hole 14 through access opening 18 in member 7. Cutter 1 may then be partially closed so that blade 8 and knife edge 15 move towards suture 5, without contacting it. This causes element 10 to meet arm 9 and secure suture 5 in hole 14. In the preferred form of the device, inclined face 16 puts increasing pressure on element 10 to affirmatively cause it to close slot 11.

The operative end of cutter 1 is moved along suture 5 until the underside of arm 9 and element 10 contact knot 6 in suture 5. This can be done entirely by feel and it is not necessary to actually see either knot 6 or incision 17.

Cutter 1 is then fully closed causing blade 8 and knife edge 15 to shear off suture 5, leaving stub 19 of the proper, predetermined length.

Figure 7:
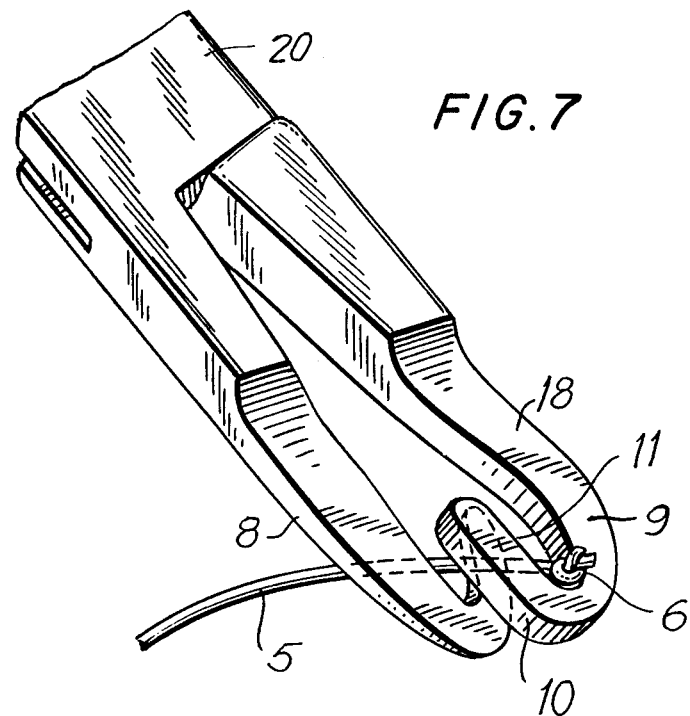
FIG. 7 is a view similar to that of FIG. 2 of another embodiment of this invention.

A modified form of the invention is shown in FIG. 7. Here slot 11 is provided with access opening 18 facing the user of the device. This permits introduction of suture 5 into slot 11 through access opening 18 from the side of the cutter away from the tissue. For some surgical procedures this form has been found particularly advantageous.

Figure 8:
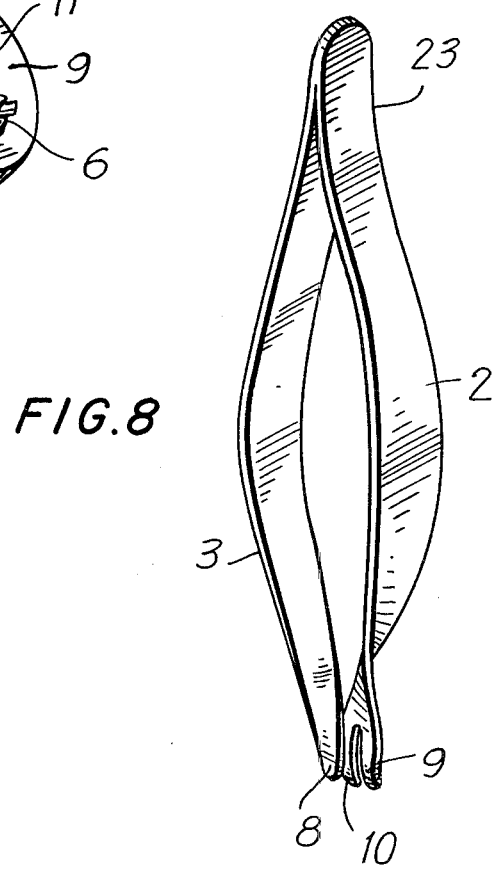
FIG. 8 is a perspective view of the "tweezer" form of the device.

It will also be appreciated that the manner of achieving the relative motion between blade 8 and member 7 is not critical. In the principal form of the invention, this has been described as a pivoted structure similar to a pair of scissors. An alternative form is shown in FIG. 8. Shanks 2 and 3 are connected by tweezer 23 thereby permitting blade 8 to shearingly contact element 10 and arm 9 in the same manner as in the other forms of the device. This embodiment has been found most useful in eye surgery and similar delicate surgical procedures.

Figure 9:
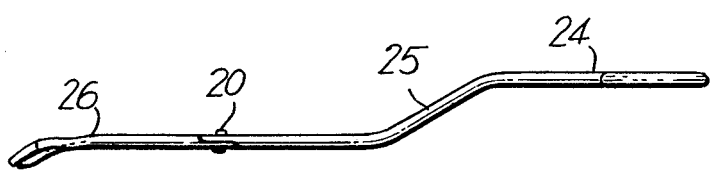
FIG. 9 is a schematic view of the "offset" form of the invention.

Sometimes the angle of use of the device is such that the head interferes with the vision of the surgeon. In such situations, the embodiment as schematically shown in in FIG. 9 may be useful. Handle section 24 is in one plane and head section 26 is in another plane. Sloping section 25 connects the two. In this form of the device, the surgeon has a better view of what he is doing and, for certain applications, will find it more convenient to use. While this embodiment has been illustrated in connection with the scissor-like form of the device, it is, of course, equally applicable to the tweezer-like device.

Figure 10:
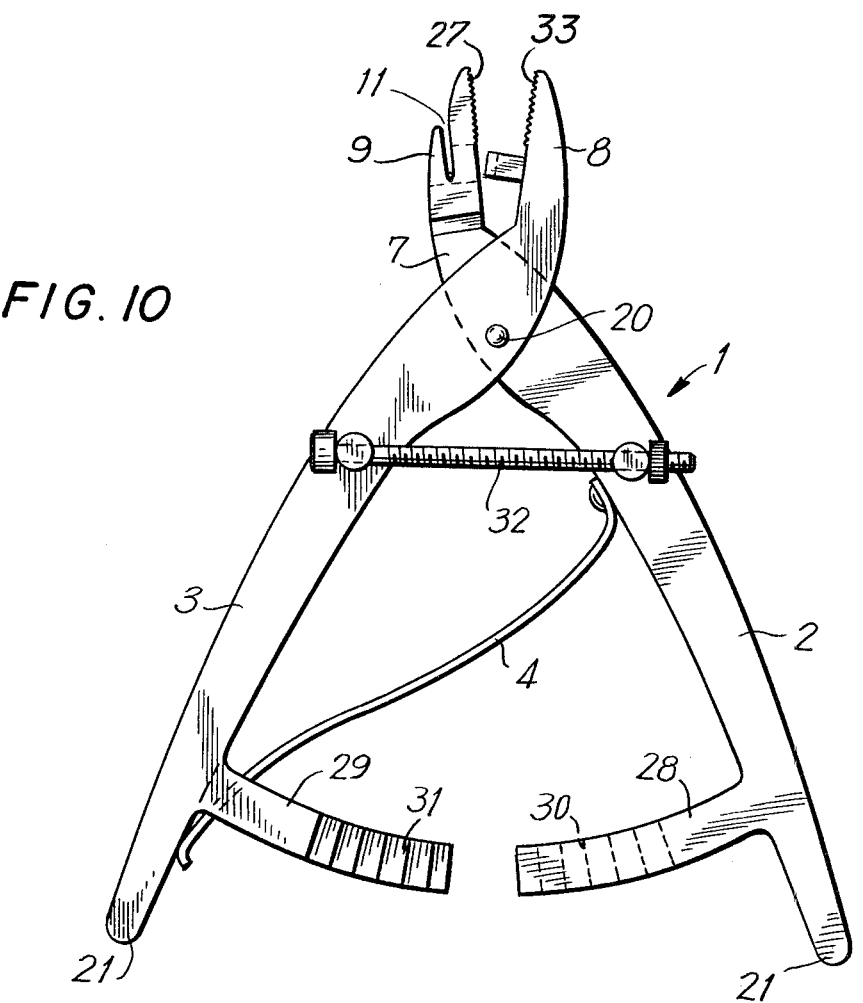
FIG. 10 is a plan view of the combination suture cutter and suture holder modification.
Figure 11:
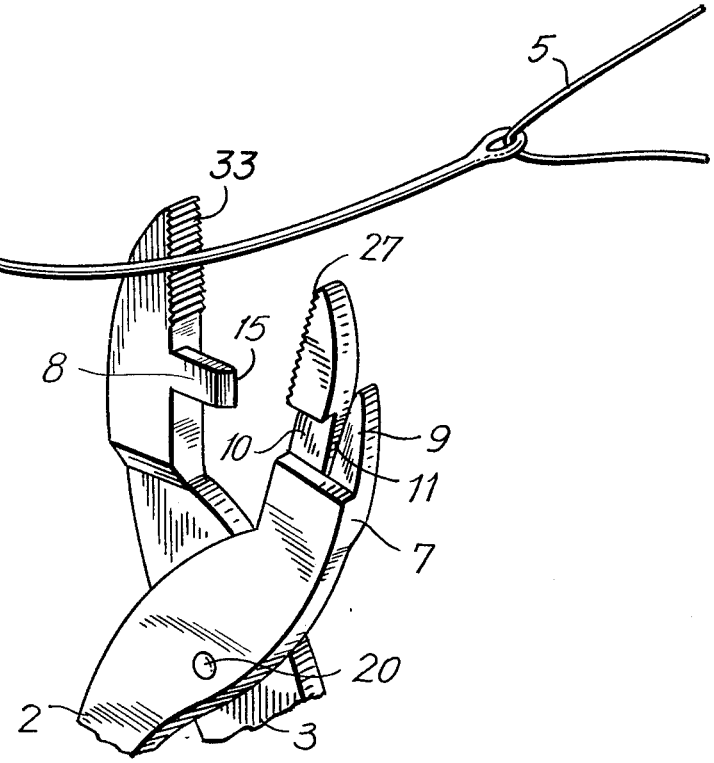
FIG. 11 is an enlarged view of the head of the suture cutter of FIG. 10.

Referring more specifically to FIGS. 10 and 11, a further modification of the present invention includes the provision of a needle holder as part of the single tool. The configuration of the device is generally the same as the other forms of the invention, but there are also provided needle-gripping areas 33 and 27 on blade 8 and member 7, respectively. Knife edge 15 is of a slightly different shape and bears against element 10 and arm 9.

The device is also provided with first grip 28 and second grip 29 on shanks 2 and 3, respectively. Grip 28 carries first ratchet 30 and grip 29 carries second ratchet 31. Ratchets 30 and 31 face each other and are adapted to inter-engage.

As the device is closed and the needle gripped between areas 27 and 33, ratchets 30 and 31 overlap one another and interlock. This holds the device in the closed position against the tension of spring 4. The surgeon then can tie the knot without danger of releasing the needle inadvertently.

After the knots have been completed, the needle is released, the thread inserted into slot 11, and the device is closed. This causes knife edge 15 to shear off the suture in a similar manner to the other embodiments of this invention. As a result, a stub equal in length to the thickness of arm 10 and element 11 is left. This form of the device enables the surgeon to make the stitch, tie the knot, and cut the thread without changing instruments.

As an additional safety feature, limit screw 32 is provided. This adjustable screw prevents the device from opening wider than is desired. For best results, knife edge 15 should remain in contact with arm 9 or element 10 at all times. This prevents any tissue from being caught between knife edge 15 and element 10.

It is one of the features of the present invention that, in its most preferred form, the instrument is so designed that knife edge 15 is not permitted to extend beyond number 7. This prevents tissue from being inadvertently caught between the knife edge and the member. Moreover, due to the inherent nature of the scissor-like action of the instrument, the blade is self-sharpening. Abrasion against the member acts to hone the edge and maintain it in sharp condition.

While only a limited number of embodiments of this invention have been specifically described, it is, nonetheless, to be broadly construed and not to be limited except by the character of the claims appended hereto.

We claim:

1. A suture cutter comprising:
   an elongated member and an elongated blade, said blade having a knife edge for shearing a suture and a back remote from said edge,
   said member having a depth and comprising an arm, an element, and a slot therebetween, said slot having a portion adapted to receive a suture but being too small to permit a knot in the suture to pass therethrough, and
   means connecting said member and said blade for relative movement therebetween in a direction substantially perpendicular to said elongated member and blade, said means enabling suture-shearing contact between said member and said blade such that said blade is relatively movable across said slot for cutting the suture so as to leave a stub on the side of the suture away from the tissue in which the suture is tied substantially equal in length to the depth of said member.

2. The suture cutter of claim 1 wherein said means resiliently connects said member and said blade to each other at a location remote from said knife edge so as to form a tweezer-like structure.

3. The cutter of claim 2 wherein said member and said blade are not in the same plane as said remote location.

4. The suture cutter of claim 1 wherein a needle gripping area is provided on each of said member and said blade.

5. A suture cutter according to claim 1, further comprising a first shank terminating at its distal end in said member and at its proximal end in a handle, and a second shank terminating at its distal end in said blade and at its proximal end in a handle, said connecting means pivotally connecting said shanks at a point intermediate their ends so as to form a scissor-like structure.

6. The cutter of claim 5 wherein said member and said blade are not in the same plane as said handles.

7. The suture cutter of claim 5 wherein a needle gripping area is provided on each of said member and said blade, each said needle gripping area being located adjacent the end of said first or second shank remote from said handle.

8. The suture cutter of claim 7, further comprising:
a first grip on said first shank and a second grip on said second shank, each of said first grip and said second grip being located between said intermediate point and handle and being adapted to overlap the other as said cutter is closed into suture-shearing contact of said member and blade,
a first ratchet on one surface of said first grip, and
a second ratchet on said second grip complementary to said first ratchet and adapted to releasably engage said first ratchet as said cutter is closed,
such that said cutter may be retained in its closed position by the interlocking of said first and second ratchets.

9. The cutter of claim 1 wherein said element is resiliently movable with respect to said arm for enabling movement of said element toward said arm under the influence of said blade so as to close said slot and secure the suture therein.

10. The cutter of claim 1 wherein said element is flexible with respect to said arm for enabling movement of said element toward said arm under the influence of said blade so as to close said slot and secure the suture therein.

11. The cutter of claims 9 or 10 wherein said blade includes a face for contact with said element as said member and blade are moved relatively together for cutting the suture, said face being inclined with respect to the area of its contact with said element for wedging action between said blade and element.

12. The cutter of claim 1 wherein said slot includes an access portion between said arm and said element for facilitating entry of the suture into said slot.

13. The cutter of claim 12 wherein said access portion is open away from said tissue.

14. The cutter of claim 13 wherein said knife edge is inclined toward said member as said edge extends in a direction away from said tissue.

15. The cutter of claim 12 wherein said access portion is flared.

16. The cutter of claim 1 wherein said slot portion includes a notch for receiving said suture and predeterminately sized to accept the suture while preventing passage through said notch of a knot in the suture.

17. A cutter according to claim 1 wherein said knife edge is angled toward said member in the direction away from the bottom of said slot, whereby said suture is urged into said slot as said suture is cut.

18. A cutter according to claim 1 wherein said knife edge is angled so that it urges said suture toward the bottom of said slot as said suture is cut.

* * * * *